US009662226B2

(12) United States Patent
Wickham (10) Patent No.: US 9,662,226 B2
(45) Date of Patent: May 30, 2017

(54) SPINAL IMPLANT SYSTEM AND METHOD (71) Applicant: Warsaw Orthopedic, Inc., Warsaw, IN (US)

(72) Inventor: Jeffrey Wickham, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/444,047

(22) Filed: Jul. 28, 2014

(65) Prior Publication Data
US 2016/0022431 A1 Jan. 28, 2016

(51) Int. Cl.
*A61F 2/44* (2006.01)
*A61F 2/30* (2006.01)

(52) U.S. Cl.
CPC ............ *A61F 2/447* (2013.01); *A61F 2/4455* (2013.01); *A61F 2002/30092* (2013.01); *A61F 2002/3092* (2013.01); *A61F 2002/3093* (2013.01); *A61F 2002/30904* (2013.01); *A61F 2002/4475* (2013.01); *A61F 2310/00017* (2013.01); *A61F 2310/00023* (2013.01); *A61F 2310/00215* (2013.01); *A61F 2310/00293* (2013.01); *A61F 2310/00359* (2013.01)

(58) Field of Classification Search
CPC ...... A61F 2/442; A61F 2/447; A61F 2/30965; A61F 2/4465; A61F 2/44; A61F 2/4455; A61F 2002/30011; A61F 2002/30013; A61F 2002/3092; A61F 2002/30383; A61F 2002/30433; A61F 2002/30517; A61F 2002/30774; A61F 2002/30785; A61F 2002/30879; A61F 2002/30909; A61F 2002/30915; A61F 2002/4475; A61F 2002/00017; A61B 17/7059
USPC .................................... 623/17.11–17.16
See application file for complete search history.

(56) References Cited

U.S. PATENT DOCUMENTS

| | | | |
|---|---|---|---|
| 5,716,415 A | 2/1998 | Steffee | |
| 7,018,416 B2 | 3/2006 | Hanson | |
| 8,496,710 B2 | 7/2013 | Bagga | |
| 8,940,052 B2 * | 1/2015 | Lechmann | A61F 2/442 606/246 |
| 8,979,934 B2 * | 3/2015 | Kirschman | A61F 2/30771 623/17.11 |
| 9,186,257 B2 * | 11/2015 | Geisler | A61F 2/442 |
| 2005/0038511 A1 | 2/2005 | Martz | |
| 2008/0161920 A1 | 7/2008 | Melkent | |
| 2009/0118836 A1 | 5/2009 | Cordaro | |
| 2011/0029087 A1 | 2/2011 | Haider et al. | |
| 2011/0224796 A1 | 9/2011 | Weiland et al. | |
| 2013/0116793 A1 * | 5/2013 | Kloss | A61F 2/442 623/17.16 |

(Continued)

OTHER PUBLICATIONS

International Search Report and the Written Opinion of the Internationalsearching Authority—International application No. PCT/US2015/039192, International filed Jul. 6, 2015 (Jul. 6, 2015) mailed from ISA/KR-Korean Intellectual Property Office, Oct. 12, 2015.

*Primary Examiner* — Pedro Philogene (57) ABSTRACT

A spinal implant is provided that comprises a first vertebral engaging surface and a second vertebral engaging surface. A wall extends between the surfaces. A lattice is disposed adjacent the wall and extending between the surfaces. Systems and methods of use are disclosed.

20 Claims, 3 Drawing Sheets (56) References Cited

U.S. PATENT DOCUMENTS

2014/0107786 A1\* 4/2014 Geisler .............. A61F 2/30965
                                                    623/17.16
2014/0277484 A1   9/2014 Prevost et al.
2014/0277505 A1\* 9/2014 Mitchell ................ A61L 27/10
                                                    623/17.16

\* cited by examiner

SPINAL IMPLANT SYSTEM AND METHOD

TECHNICAL FIELD

The present disclosure generally relates to medical devices for the treatment of musculoskeletal disorders, and more particularly to a surgical system and method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, interbody implants can be delivered to a surgical site for fixation with bone to immobilize a joint. This disclosure describes an improvement over these prior art technologies.

SUMMARY

In one embodiment, a spinal implant is provided that comprises a first vertebral engaging surface and a second vertebral engaging surface. A wall extends between the surfaces. A lattice is disposed adjacent the wall and extending between the surfaces. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

The exemplary embodiments of the surgical system and related methods of use disclosed are discussed in terms of medical devices for the treatment of musculoskeletal disorders and more particularly, in terms of a surgical system including a spinal implant and a method for treating a spine. In one embodiment, the systems and methods of the present disclosure are employed with a spinal joint fusion, for example, with a cervical, thoracic, lumbar and/or sacral region of a spine. In one embodiment, the spinal implant includes an interbody device, a plate and/or bone fasteners.

In some embodiments, the present system comprises a spinal implant including a lattice and a frame porous titanium interbody implant with an optimized modulus. In some embodiments, the present system comprises a spinal implant including a titanium implant. In some embodiments, the present system comprises a spinal implant including a lattice and a frame titanium interbody device with an optimized modulus that may be more efficiently manufactured using additive manufacturing techniques.

In some embodiments, the spinal implant includes an interbody spacer having a modulus in a range of the modulus of bone to reduce a risk of stress shielding in the interbody spacer. In some embodiments, the spinal implant includes an interbody spacer that combines a low modulus with ossification-enabling characteristics and bony ingrowth features that mechanically lock the implant to bone. In some embodiments, the spinal implant combines a modulus similar to bone, bony ongrowth, bony ingrowth and mechanical robustness. In some embodiments, the spinal implant includes an interbody spacer having a porous lattice contained within a frame.

In some embodiments, the frame includes external features such as teeth and corners. In some embodiments, the frame includes continuous faces for marking. In some embodiments, the frame includes a shell for a lattice of a frame so that no thin projections from the lattice are exposed. In some embodiments, the lattice includes a reduced modulus. In some embodiments, the lattice provides for bony ingrowth. In some embodiments, the lattice provides predictable pore placement under teeth of the interbody implant to minimize the distance that bone can grow before it interlocks with the implant. In some embodiments, the lattice provides predictable structural support placement within the implant.

In some embodiments, the spinal implant includes a porous titanium interbody spacer with bony ingrowth features and a modulus approximating bone. In some embodiments, the spinal implant includes teeth having solid tips. In some embodiments, the spinal implant includes pores positioned below teeth tips. In some embodiments, the spinal implant includes at least one solid face for marking. In some embodiments, the spinal implant includes solid corners for robustness. In some embodiments, the spinal implant includes at least one sight window. In some embodiments, the spinal implant includes a framework having an outer frame and an internal lattice.

In some embodiments, the spinal implant includes an interbody spacer having a modulus of elasticity in a range of approximately 300 megapascal (MPa) to approximately 12000 MPa. In some embodiments, the spinal implant includes an interbody spacer having a modulus of elasticity in a range of approximately 2 gigapascal (GPa) to approximately 3 GPa. In some embodiments, the spinal implant includes an interbody spacer having a lattice with openings completely through its frame. In some embodiments, the spinal implant includes an interbody spacer having a lattice with openings, such as, for example, lattice holes having a 0.75 millimeter (mm) diameter.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

Figure 1:
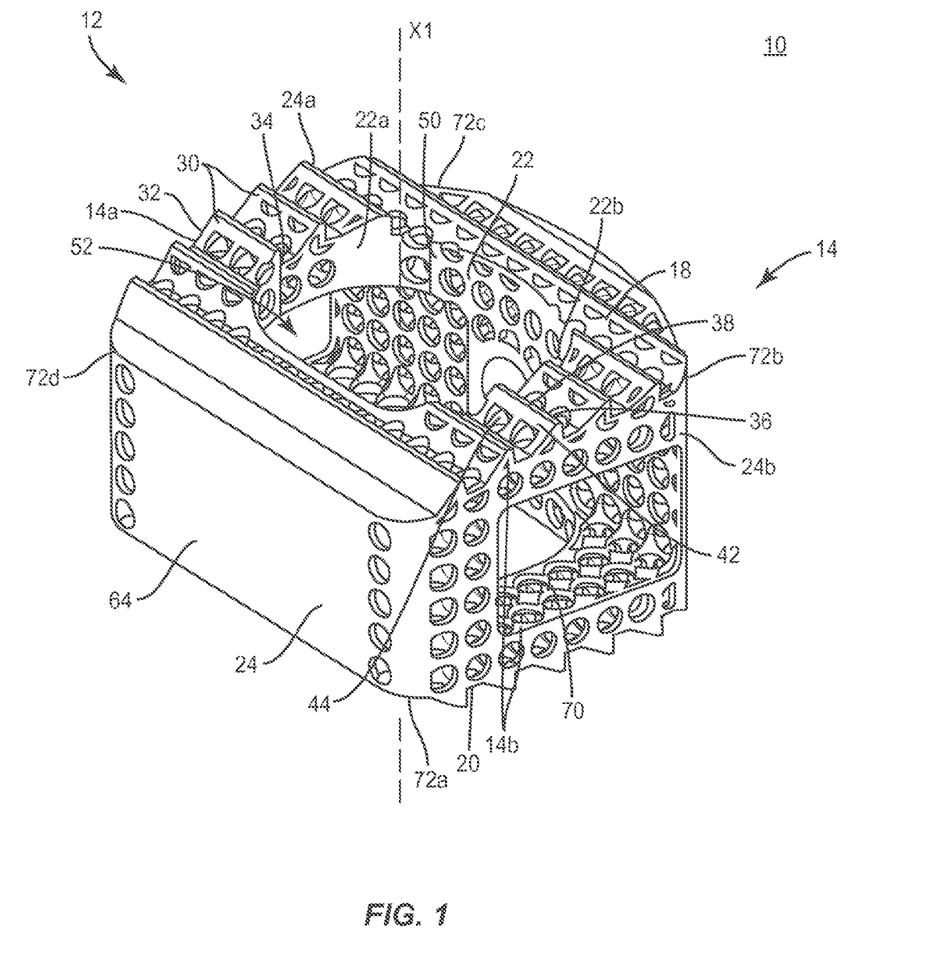
FIG. 1 is a perspective view of components of one embodiment of a system in accordance with the principles of the present disclosure.
Figure 2:
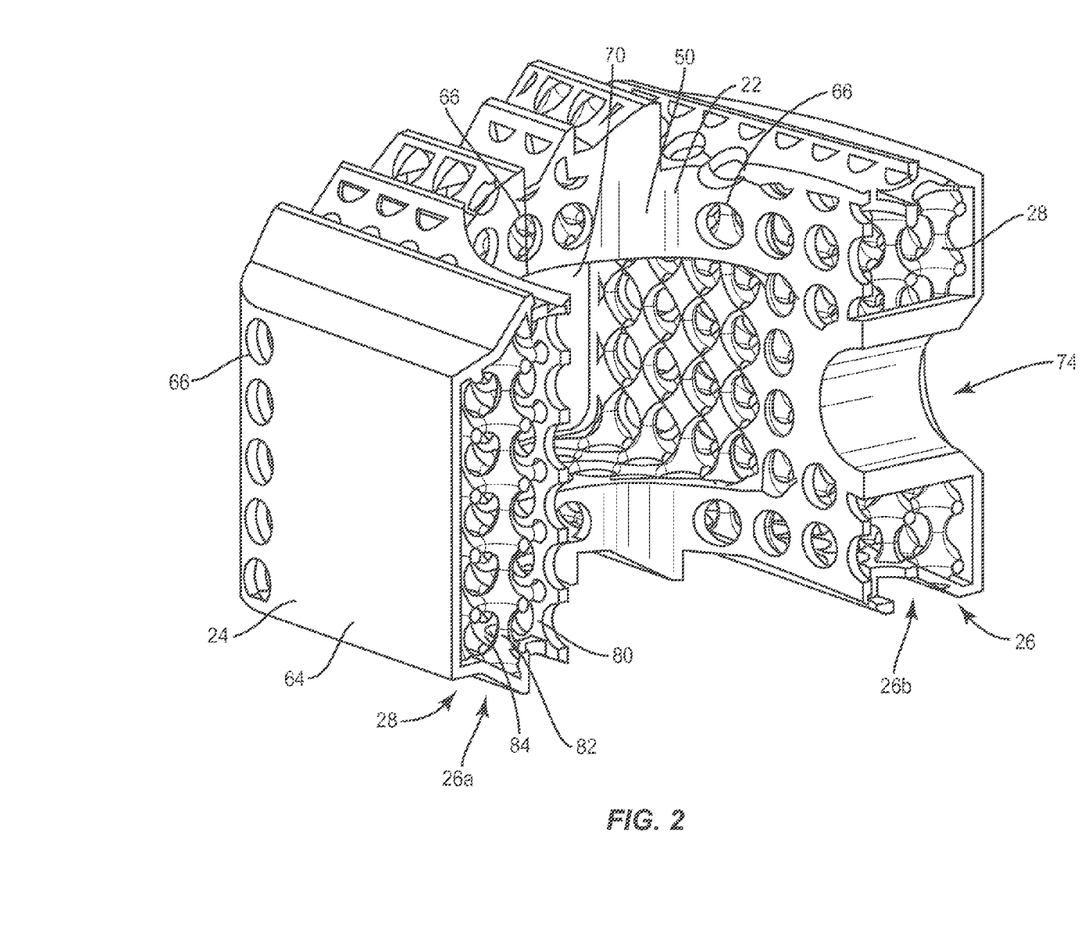
FIG. 2 is an enlarged cutaway view of the components shown in FIG. 1.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1 and 2, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-(3), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques and/or mini-open surgical techniques to deliver and introduce instrumentation and/or implants, such as, for example, an interbody implant, at a surgical site within a subject body of a patient, which includes, for example, a spine. In some embodiments, the implant can include spinal constructs including one or more bone fasteners, spinal rods, connectors and/or plates. In some embodiments, various components of spinal implant system 10 may be utilized in open or traditional spinal surgical techniques.

Spinal implant system 10 includes an interbody implant 12. Interbody implant 12 has an implant body that defines a longitudinal axis X1. The implant body comprises a frame 14 including at least a portion of a vertebral engaging surface 18 and a vertebral engaging surface 20. In some embodiments, the cross-section geometry of frame 14 may have various configurations, such as, for example, cylindrical, oval, oblong, triangular, polygonal having planar or arcuate side portions, irregular, uniform, non-uniform, consistent, variable, horseshoe shape, U-shape or kidney bean shape. In some embodiments, surface 18 and/or surface 20 may be rough, textured, porous, semi-porous, dimpled, knurled, toothed, grooved and/or polished to facilitate engagement with tissue. In some embodiments, the vertebral tissue may include intervertebral tissue, endplate surfaces and/or cortical bone. In some embodiments, all or only a portion of interbody implant 12 includes, is fabricated from and/or is coated with titanium.

Frame 14 includes an inner wall 22 that extends between surfaces 18, 20. Frame 14 includes an outer wall 24 that extends between surfaces 18, 20. Walls 22, 24 are spaced apart between surfaces 18, 20 and define one or more cavities 26 disposed between walls 22, 24. In some embodiments, wall 22 includes a portion 22a and wall 24 includes a portion 24a, which comprise a side frame 14a of frame 14. Portions 22a, 24a are spaced apart to define a portion of cavity 26 and connect end portions of frame 14 via side frame or bridge 14a. In some embodiments, wall 22 includes a portion 22b and wall 24 includes a portion 24b, which comprise a side frame 14b of frame 14. Portions 22b, 24b are spaced apart to define a portion of cavity 26 and connect end portions of frame 14 via side frame or bridge 14b.

Cavity 26 is configured for disposal of a lattice 28, as described herein. In some embodiments, cavity 26 may include one or a plurality of open and/or closed sections, which may communicate. In some embodiments, all or only a portion of cavity 26 may include a cross-section configuration, such as, for example, cylindrical, oval, oblong, triangular, polygonal having planar or arcuate side portions, irregular, uniform, non-uniform, consistent and/or variable. In some embodiments, all or only a portion of cavity 26 may be uniform, undulating, tapered, increasing, decreasing, variable, offset, arcuate, angled and/or staggered. In some embodiments, wall 22 and/or wall 24 may be rough, textured, porous, semi-porous, dimpled, knurled, toothed, grooved and/or polished. In some embodiments, wall 22 and/or wall 24 define a thickness, which may be uniform, undulating, tapered, increasing, decreasing, variable, offset, stepped, arcuate, angled and/or staggered.

Cavity 26 includes an end portion 26a and an end portion 26b, as shown in FIG. 2, configured for disposal of one or more portions of lattice 28. In some embodiments, lattice 28 may include one or more portions, layers and/or substrates. In some embodiments, one or more portions, layers and/or substrates of lattice 28 may be disposed side by side, offset, staggered, stepped, tapered, end to end, spaced apart, in series and/or in parallel. In some embodiments, lattice 28 defines a thickness, which may be uniform, undulating, tapered, increasing, decreasing, variable, offset, stepped, arcuate, angled and/or staggered.

In some embodiments, one or more layers of lattice 28 are disposed in a side by side, parallel orientation within cavities 26a, 26b and extend between surfaces 18, 20. Lattice 28 includes one or more layers of a matrix of material, such as, for example, a latticework 80. Latticework 80 includes a plurality of nodes 82 and openings 84 disposed in rows and columns and/or in series and parallel. Latticework 80 is disposed between walls 22, 24 and surfaces 18, 20 to reduce density of the implant body of interbody implant 12. This configuration provides a low modulus of elasticity to the implant body of interbody implant 12 and increases flexibility.

In some embodiments, lattice 28 provides a low modulus of elasticity to the implant body of interbody implant 12 in a range of the modulus of bone. In some embodiments, frame 14 has a modulus of elasticity in a range of approximately 300 MPa to approximately 12000 MPa. In some embodiments, frame 14 has a modulus of elasticity in a range of approximately 2 GPa to approximately 3 GPa. In some embodiments, nodes 82 and openings 84 may be disposed in a diagonal orientation. In some embodiments, openings 84 extend completely through frame 14. In some embodiments, openings 84 have a 0.75 mm diameter.

Wall 24 includes continuous and uninterrupted faces, such as, for example, solid corners 72a, 72b, 72c, 72d. The configuration of corners 72a, 72b, 72c, 72d with wall 24 provides strength and robustness to the implant body of interbody implant 12.

The implant body of interbody implant 12 includes a tissue penetrating member, such as, for example, a tooth 30 disposed transversely along surface 18 and/or surface 20, as shown in FIG. 1. In one embodiment, implant 12 includes a plurality of teeth 30. In one embodiment, teeth 30 may have various configurations, for example, parallel, converging, diverging, irregular, tapered, offset, staggered, uniform and non-uniform.

Each tooth 30 includes a portion 32 and a portion 34 that connect to form a cutting surface 36. Surface 36 is configured to engage endplate tissue, such as, for example, soft tissues, bone and/or fluids to cut, shave, shear, incise and/or remove such tissue. Surface 36 includes a cutting tip, such as, for example, a solid cutting tip 38. Each tooth 30 includes a surface 42 that defines at least one opening 44. In some embodiments, one or more openings 44 are configured to form a porous tooth surface adjacent tip 38. In some embodiments, at least one opening 44 guides, drives and/or directs the tissue cut by surface 36, and/or other tissue and bone growth promoting material adjacent the surfaces of the implant body of interbody implant 12.

In some embodiments, teeth 30 may be disposed in a serial and/or overlapping configuration to provide a matrix of teeth 30. In some embodiments, teeth 30 are disposed along surface 18 and/or surface 20 such that cut osteogenic tissue and/or other bone growth promoting material create a mechanical interlock of the implant body of interbody implant 12 with a vertebral endplate and/or form a scaffold for bone growth.

Wall 22 includes a surface 50 that defines an opening, such as, for example, an axial opening 52 configured to receive an agent, which may include bone graft (not shown) and/or other materials, as described herein, for employment in a fixation or fusion treatment.

Wall 24 includes openings 66 disposed in columns and rows thereabout. Openings 66 are configured for disposal of tissue and/or other bone growth promoting material, which may include cut osteogenic tissue, to create a mechanical interlock of the implant body of interbody implant 12 with a vertebral endplate and/or form a scaffold for bone growth to facilitate fixation and fusion. Walls 22, 24 define openings, such as, for example, windows 70 configured to facilitate positioning and disposal of an agent, which may include bone graft and/or other materials, as described herein. Walls 22, 24 define an opening 74 configured to facilitate engagement with a surgical tool or instrument for positioning and alignment of the implant body of interbody implant 12 with tissue, as described herein.

Wall 24 includes a continuous and uninterrupted face, such as, for example, a solid face 64. In some embodiments, face 64 is configured for disposal of visual indicia. In one embodiment, the visual indicia is configured to provide configuration and/or a dimension of interbody implant 12. In some embodiments, system 10 may comprise a kit including a plurality of implants with visual indicia indicative of their respective configuration and dimension. In some embodiments, the visual indicia may include color coding to provide configuration and/or a dimension of interbody implant 12.

Figure 3:
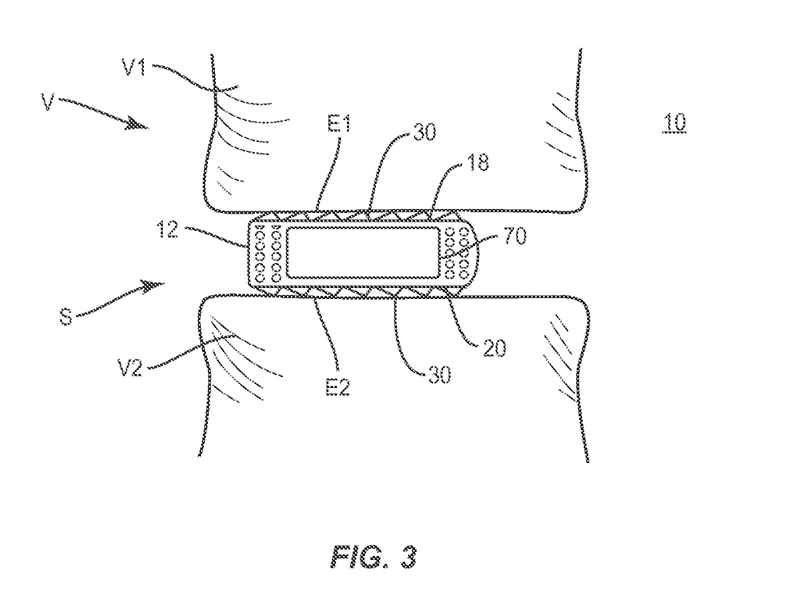
FIG. 3 is a side view of the components shown in FIG. 1 disposed with vertebrae.

In assembly, operation and use, as shown in FIG. 3, spinal implant system 10, similar to the systems and methods described herein, is disposed with tissue, such as, for example, vertebrae V for treatment of a spinal disorder, such as those described herein, affecting a section of a spine of a patient. Spinal implant system 10 may also be employed with other surgical procedures.

To treat the affected section of vertebrae V, an incision is made with a surgical instrument, such as, for example, a scalpel. In some embodiments, a discectomy is performed adjacent the intervertebral space. In some embodiments, sequential trial implants are delivered and used to distract the intervertebral space and apply appropriate tension in the intervertebral space allowing for indirect decompression. In some embodiments, the size of interbody implant 12 is selected after trialing. In some embodiments, interbody implant 12 is visualized by fluoroscopy and oriented before malleting into the intervertebral space.

An inserter (not shown) is connected with interbody implant 12 via opening 74 to direct interbody implant 12 between vertebrae V1, V2 such that surface 18 is disposed in a cephalad orientation of the body and surface 20 is disposed in a caudal orientation of the body. The inserter delivers interbody implant 12 through the incision to a surgical site for implantation into the intervertebral space S between vertebrae V1, V2.

As interbody implant 12 is inserted into space S, teeth 30 translate along the surface of endplate E1 and/or endplate E2. Translation of teeth 30 along the surfaces of endplate E1 and/or endplate E2 cause teeth 30 and/or surfaces 18, 20 to engage the soft tissues, bone and/or fluids of endplate E1 and/or endplate E2 for forming a mechanical lock of interbody implant 12 with vertebrae V1, V2. In an implanted position, as shown in FIG. 3, surface 18 engages endplate tissue of endplate E1 and surface 20 engages endplate tissue E2.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A spinal implant comprising:
   a first vertebral engaging surface;
   a second vertebral engaging surface;
   a wall extending continuously from the first vertebral engaging surface to the second vertebral engaging surface; and
   a lattice disposed adjacent the wall and extending between the engaging surfaces such that the engaging surfaces cover top and bottom portions of the lattice.
2. A spinal implant as recited in claim 1, wherein the spinal implant comprises an implant body including titanium.
3. A spinal implant as recited in claim 1, wherein at least a portion of the lattice is porous.
4. A spinal implant as recited in claim 1, wherein the spinal implant comprises an implant body including a modulus of elasticity in a range of 300 MPa to 12000 MPa.
5. A spinal implant as recited in claim 1, wherein the wall includes an outer wall and an inner wall such that the lattice is disposed between the walls.
6. A spinal implant as recited in claim 1, wherein the wall includes a frame that defines a cavity configured for disposal of the lattice.
7. A spinal implant as recited in claim 1, wherein the lattice includes a first layer and a second layer.
8. A spinal implant as recited in claim 1, wherein the wall includes a face having a continuous and uninterrupted face to fix the first vertebral engaging surface relative to the second vertebral engaging surface.
9. A spinal implant as recited in claim 1, wherein the wall includes a solid face.
10. A spinal implant as recited in claim 1, wherein the spinal implant comprises an implant body having a plurality of corners such that the wall is solid adjacent the corners.
11. A spinal implant as recited in claim 1, wherein the spinal implant comprises an implant body including at least one window.
12. A spinal implant as recited in claim 1, wherein the wall includes a face that defines a plurality of openings.
13. A spinal implant as recited in claim 1, wherein at least one of the surfaces includes at least one tissue penetrating member.
14. A spinal implant as recited in claim 1, wherein at least one of the surfaces includes a plurality of teeth extending transversely therealong.

15. A spinal implant as recited in claim 1, wherein at least one of the surfaces includes at least one tissue penetrating member having a solid tip extending transversely along the surface.

16. A spinal implant as recited in claim 1, wherein at least one of the surfaces includes at least one tissue penetrating member having a porous surface disposed adjacent a tip.

17. A spinal implant comprising:

a frame including a first vertebral engaging surface and a second vertebral engaging surface, the frame further including an inner wall that defines an axial opening and an outer wall, the walls defining at least one cavity therebetween, at least a portion of the outer wall extending continuously from the first vertebral engaging surface to the second vertebral engaging surface; and a porous lattice disposed within the at least one cavity and extending between the engaging surfaces such that the engaging surfaces cover top and bottom portions of the lattice.

18. A spinal implant as recited in claim 17, wherein the frame includes titanium.

19. A spinal implant as recited in claim 17, wherein the frame includes a modulus of elasticity in a range of 300 MPa to 12000 MPa.

20. A spinal implant comprising:

a titanium body including a first vertebral engaging surface and a second vertebral engaging surface, at least one of the surfaces including a plurality of tissue penetrating members engageable with a vertebral endplate;

a wall extending continuously from the first vertebral engaging surface to the second vertebral engaging surface; and a lattice disposed adjacent the wall and extending between the surfaces such that the surfaces completely cover opposite top and bottom portions of the lattice.

* * * * *

UNITED STATES PATENT AND TRADEMARK OFFICE
CERTIFICATE OF CORRECTION

PATENT NO. : 9,662,226 B2  
APPLICATION NO. : 14/444047  
DATED : May 30, 2017  
INVENTOR(S) : Wickham It is certified that error appears in the above-identified patent and that said Letters Patent is hereby corrected as shown below:

In the Specification

In Column 4, Line 33, delete "TGF-(3)," and insert -- TGF-β), --, therefor.

In Column 5, Line 39, delete "dosed" and insert -- closed --, therefor.

Signed and Sealed this
First Day of August, 2017

Joseph Matal
*Performing the Functions and Duties of the*
*Under Secretary of Commerce for Intellectual Property and*
*Director of the United States Patent and Trademark Office*